(12) United States Patent
Kremp et al.

(10) Patent No.: US 9,766,396 B2
(45) Date of Patent: Sep. 19, 2017

(54) HIGH BACKSCATTERING WAVEGUIDES

(71) Applicant: OFS Fitel, LLC, Norcross, GA (US)

(72) Inventors: Tristan Kremp, Somerset, NJ (US); Paul S Westbrook, Bridgewater, NJ (US); Tommy Geisler, Brondby (DK)

(73) Assignee: OFS FITEL, LLC, Norcross, GA (US)

( * ) Notice: Subject to any disclaimer, the term of this patent is extended or adjusted under 35 U.S.C. 154(b) by 0 days.

(21) Appl. No.: 15/175,656

(22) Filed: Jun. 7, 2016

(65) Prior Publication Data

US 2016/0356709 A1    Dec. 8, 2016

Related U.S. Application Data

(60) Provisional application No. 62/172,336, filed on Jun. 8, 2015.

(51) Int. Cl.
*G02B 6/02*    (2006.01)

(52) U.S. Cl.
CPC .................. *G02B 6/02* (2013.01)

(58) Field of Classification Search
CPC ........................................... G02B 6/02
See application file for complete search history.

(56) References Cited

U.S. PATENT DOCUMENTS 5,848,204 A * 12/1998 Wanser ............... G01L 1/246
                                                    385/12
2014/0263985 A1    9/2014 Westbrook

OTHER PUBLICATIONS

Loranger, S. et al., "Rayleigh scatter based order of magnitude increase in distributed temperature and strain sensing by simple UV exposure of optical fibre," Scientific Reports 5, 11177; doi: 10.1038/srep11177 (2015).

* cited by examiner

*Primary Examiner* — Ryan Lepisto
(74) *Attorney, Agent, or Firm* — Sam S. Han, Esq.

(57) ABSTRACT

A high backscattering fiber comprising a perturbed segment in which the perturbed segment reflects a relative power that is more than three (3) decibels (dB) above Rayleigh scattering. The high backscattering fiber also exhibits a coupling loss of less than 0.5 dB.

11 Claims, 8 Drawing Sheets

HIGH BACKSCATTERING WAVEGUIDES

CROSS REFERENCE TO RELATED APPLICATIONS

This application claims the benefit of U.S. provisional patent application Ser. No. 62/172,336, filed 2015 Jun. 8, by Kremp and Westbrook, having the title "High Backscattering Fiber," which is incorporated herein by reference in its entirety.

BACKGROUND

Field of the Disclosure

The present disclosure relates generally to waveguides and, more particularly, to high backscattering waveguides.

Description of Related Art

Various optical sensing methods rely on measurements of backscattered signals from a waveguide to determine physical quantities such as temperature or strain along the waveguide. For example, in optical frequency domain reflectometry (OFDR) or optical time domain reflectometry (OTDR), temperatures or strains along an optical fiber can be measured based on backscattering. To improve the accuracy and repetition rates of these measurements, there are ongoing efforts to improve the signal-to-noise ratio (SNR) of the backscattered signal.

SUMMARY

The present disclosure provides high backscattering waveguides (e.g., optical fibers) and sensors employing high backscattering optical fibers. Briefly described, one embodiment comprises a high backscattering fiber that reflects a relative power that is more than three (3) decibels (dB) above the Rayleigh scattering. For some embodiments, the high backscattering fiber also exhibits a coupling loss of less than 0.5 dB.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE EMBODIMENTS

Figure 1A:
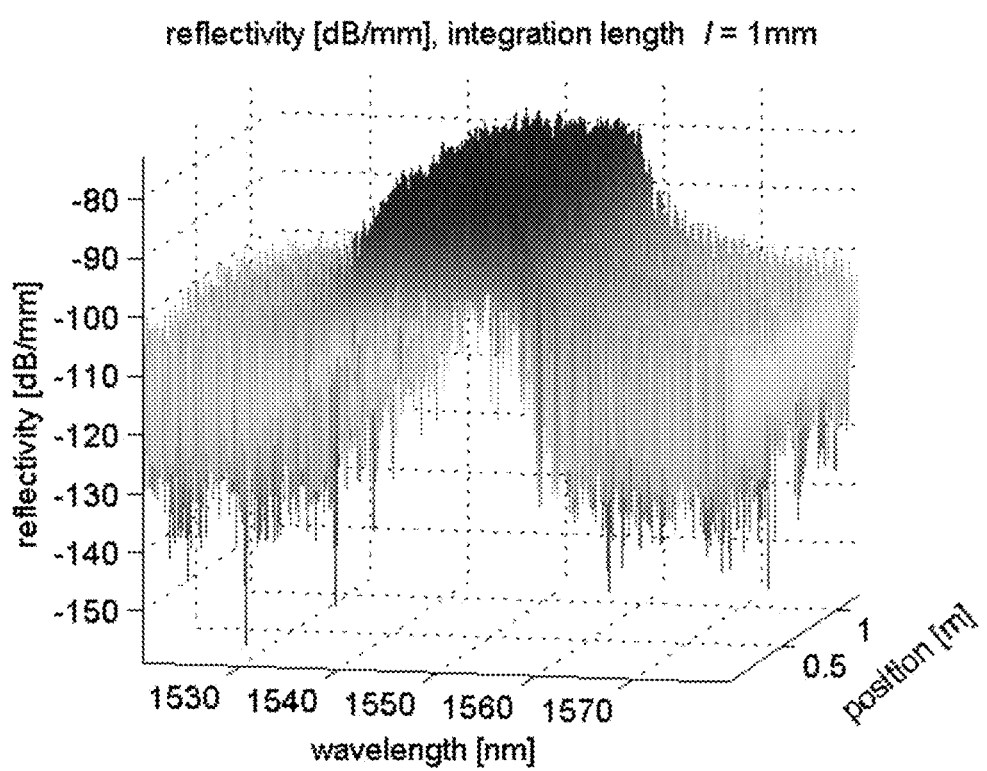
FIGS. 1A and 1B are graphs showing the reflectivity for one embodiment in which the integration length is one (1) millimeter (mm) in a 119.5 centimeter (cm) long fiber section with a design level of −80 decibel (dB) backscatter per 1 mm (1/mm) in a wavelength range of 1550±7.5 nanometers (nm). The shortest integration length, for which the backscatter enhancement persists over the full measurement (e.g., OFDR or OTDR) bandwidth, is an approximate lower bound for the achievable spatial resolution of the measurement system.

Rayleigh scattering (both forward scattering and backscattering) occurs in all optical fibers, and is a well-documented phenomenon. Typical optical fibers exhibit random refractive index fluctuations at scales of tens of nanometers. These fluctuations are responsible for so-called Rayleigh scattering, which arises from thermal fluctuations that are frozen into the fiber during the draw process. Their presence gives rise to both a back scattered signal for core-guided light, which is useful for many sensing applications, as well as light scattering to non-guided light, which results in losses for transmitted light. The Rayleigh scattering is usually very broadband and has a relatively low intensity that is approximately (in the limit of very small scattering centers) proportional to the inverse fourth power ($\lambda^{-4}$) of the wavelength ($\lambda$).

Physical quantities such as temperature and strain along an optical fiber are measureable using optical sensing methods that measure Rayleigh backscattering, such as optical frequency domain reflectometry (OFDR) and optical time domain reflectometry (OTDR). As in most measurements, high signal-to-noise ratio (SNR) provides greater accuracy and higher repetition rates.

One way of increasing the SNR of the backscattered signal is by increasing core dopant levels to enhance density fluctuations that give rise to Rayleigh scattering and increase the measurable backscattering. However, increasing core dopant levels increases the overall loss of the fiber, thereby by limiting the achievable SNR. Additionally, increased dopant levels reduce design flexibility that is oftentimes required for complex fiber profiles, such as multi-core fibers, low birefringence fibers, fibers with polarization maintaining properties and other demanding designs. Because these complex designs require precise control of modal effective index, core placement, symmetry, eccentricity, and ovality of the fiber core, controlling backscatter by increasing dopant levels is difficult and sometimes results in optical signals being transported over the same lossy waveguide that is used for sensing the backscatter.

High backscattering optical fibers and the sensors with high backscattering fibers, as disclosed herein, provide solutions that increase backscatter without significantly affecting other properties of the waveguide. This is accomplished by altering or modifying the refractive index by applying an appropriate spatial pattern that creates a refractive index perturbation, which: (a) causes a reflectivity that is greater than three (3) or preferably greater than ten (10) decibels (dB) above Rayleigh scattering within one or more ranges of desired wavelengths (in-band) (for both single and multiple wavelength windows); but (b) maintains signal integrity and exhibits a coupling loss with a standard single-mode or multimode fiber of less than 0.5 dB, or preferably less than 0.2 dB. In other words, by applying an appropriate spatial pattern, such as a longitudinal perturbation induced by ultraviolet (UV) light in the refractive index of the core, the high backscattering optical fiber can attain a backscattered signal (within a desired range or multiple desired ranges of wavelengths (in-band) and at a desired longitudinal resolution length) that is at least 3 dB, or preferably at least 10 dB, above the Rayleigh backscatter observed outside of the desired range (out-of-band) at the desired longitudinal resolution length. As shown in greater detail below, the ratio of optical backscatter to the power that is lost in transmission (averaged over the in-band) is more than two (2) times, preferably ten (10) times the value measured for standard single-mode fibers that rely only on Rayleigh backscattering.

One way of modifying the refractive index profile is by subjecting the optical fiber waveguide to actinic radiation. Actinic radiation can include UV, IR or other electromagnetic radiation. When subjected to such actinic radiation, the refractive index of the optical waveguide is modified. Such modifications can increase the back scattering of light guided by the waveguide. The spectrum of the enhanced backscatter depends on the spatial structure of the refractive index modification. For instance, exposure to a modulated or unmodulated UV beam can cause a broadband increase of the backscatter. In contrast, a narrowband increase of the backscatter requires that the product of photosensitivity and dosage (time integral of the intensity) of the actinic radiation varies along the waveguide. More precisely, if the spatial Fourier transform (along a certain length l in direction parallel to the waveguide and in the neighborhood of the longitudinal position z) of this product has a significant components at the period $\lambda/(2n_{eff})$, which is half the wavelength of the guided light (i.e., free space wavelength $\lambda$ divided by double the effective index of the waveguide), then the guided light will experience increased back reflection over what such light would experience in an unexposed waveguide at this position z. For instance, if a UV beam with a wavelength of 200 nm is directed onto a fiber waveguide such that the accumulated dosage of the UV beam varies along the waveguide axis with a period of about 500 nm, then the resulting refractive index modification would result in increased scatter for guided light with a wavelength near 1000 nm. For a silica waveguide, such a wavelength would correspond to approximately a 1500 nm vacuum wavelength. Spatial variations may be imposed on the actinic beam through various optical techniques, e.g., interference patterns from phase masks, point-by-point inscription, diffuse scattering elements, and femtosecond systems.

Having generally described a high backscattering fiber that does not significantly affect other waveguide properties, specific embodiments of high backscattering fibers, along with their design criteria, are explained in greater detail below, making reference to the drawings to illustrate the achievable results of such a high backscattering fiber. While several embodiments are described herein, there is no intent to limit the disclosure to the embodiment or embodiments disclosed herein. On the contrary, the intent is to cover all alternatives, modifications, and equivalents.

For purposes of illustration, in one embodiment, a high backscattering fiber is described, which is capable of propagating a signal (p) and counter-propagating a reflected signal (r). The longitudinal axis of the fiber is designated as z, while the transverse axes, which are perpendicular to the waveguide axis, are designated as x and y.

Without loss of generality, we write the total refractive index profile $n^{(total)}(x, y, z)$ of the high backscattering fiber as the sum of a z-independent term $n_{x,y}(x, y)$ and a z-dependent term $\Delta n^{(total)}(x, y, z)$:

$$n^{(total)}(x,y,z) = n_{x,y}(x,y) + \Delta n^{(total)}(x,y,z). \quad (1)$$

Since any perturbation of the refractive index profile of the fiber adds to any Rayleigh scattering that already exists in the fiber, the term $\Delta n^{(total)}(x, y, z)$ in Eq. (1) is the sum of the refractive index fluctuation $\Delta n^{(Rayleigh)}(x, y, z)$ that gives rise to Rayleigh scattering, and an additional refractive index perturbation $\Delta n(x, y, z)$:

$$\Delta n^{(total)}(x,y,z) = \Delta n^{(Rayleigh)}(x,y,z) + \Delta n(x,y,z). \quad (2)$$

Those having skill in the art will appreciate that the z-dependent perturbation term $\Delta n(x, y, z)$ in Eq. (2) can be applied independently of other fiber fabrication steps, such as during or after fiber draw. In particular, certain sections of the fiber can have $\Delta n=0$.

To keep the mathematical modeling as simple as possible, we assume that the perturbation term $\Delta n$ in Eq. (2) can be written as the product of two terms that separately depend on the transverse coordinates (x, y) and on the longitudinal position z:

$$\Delta n(x,y,z) = \Delta n_{x,y}(x,y) \cdot \Delta n_z(z). \quad (3)$$

In other words, we assume that the (x, y)-dependence of the refractive index perturbation term does not change along z, if this assumption is not valid, e.g., in presence of fiber fabrication inaccuracies or tapering, a high backscattering fiber is still possible, but the mathematical modeling (see Eqs. (5/6) below) would be more involved.

Combining Eqs. (1-3), we obtain the total refractive index distribution $$n^{(total)}(x,y,z) = n_{x,y}(x,y) + \Delta n^{(Rayleigh)}(x,y,z) + \Delta n_{x,y}(x,y)\Delta n_z(z). \quad (4)$$

With $E_p(x, y)$ and $n_{eff,p}$, respectively, we denote an eigenmode and a corresponding effective index of the waveguide that is described by the z-independent refractive index profile $n_{x,y}(x, y)$ in Eq. (1). An example is the fundamental mode $p=LP_{0,1}$ of a cylindrical optical fiber. To further simplify the following mathematical description, we assume that the presence of the z-dependent refractive index term $\Delta n^{(total)}(x, y, z)$ does not significantly change the eigenmodes and effective indices. If this assumption is not valid, e.g., in the case of strong refractive index perturbations along a short section of the waveguide, a high backscattering fiber is still possible, but the mathematical modeling (see Eqs. (5/6) below) would be more involved.

With $R_{p \to r}(\lambda, z, l)$, we denote the relative amount of power that is being reflected per unit length from fiber mode $E_p$ to a counter-propagating mode $E_r$ at wavelength $\lambda$ due to the additional refractive index perturbation $\Delta n(x, y, z)$ in a section of length l at position z. $R_{p \to r}(\lambda, z, l)$ has the unit 1/m, so it is actually a reflectivity density, but, for convenience, we sometimes refer to it as the "relative reflected power," "reflectivity," or "enhanced backscatter," respectively. If the chosen integration length l is sufficiently short or if $\Delta n(x, y, z)$ in Eq. (3) is sufficiently weak, then multipath interference (MPI) effects along the length l can be neglected, and the relative reflected power $R_{p \to r}(\lambda, z, l)$ from a sole section of length l is approximately given by:

$$R_{p \to r}(\lambda, z, l) \approx \frac{1}{l}\left|\mu_{p,r}\frac{2\pi}{\lambda}\int_{z-\frac{l}{2}}^{z+\frac{l}{2}}\Delta n_z(z')e^{i2\pi z'\frac{n_{eff,p}+n_{eff,r}}{\lambda}}dz'\right|^2, \quad (5)$$

with $n_{eff,p}$ representing the effective index of the forward propagating mode $E_p$, and $n_{eff,r}$ representing the effective index of the backward propagating mode $E_r$. Numerically, the integral in Eq. (5) can be evaluated efficiently using a Fast Fourier Transform (FFT) algorithm. The modal overlap coefficient $\mu_{p,r}$ in Eq. (5) is defined as $$\mu_{p,r} := \frac{\iint_{-\infty}^{\infty} E_p(x,y) \Delta n_{x,y}(x,y) E_r^*(x,y) \, dx \, dy}{\sqrt{\iint_{-\infty}^{\infty} |E_p(x,y)|^2 \, dx \, dy} \sqrt{\iint_{-\infty}^{\infty} |E_r(x,y)|^2 \, dx \, dy}}, \quad (6)$$

where the asterisk symbol (*) represents a complex conjugate. This modal overlap coefficient $\mu_{p,r}$ summarizes the mode-coupling-related transverse properties of the two considered modes $E_p$ and $E_r$ and the refractive index distribution. $R_{p \to r}(\lambda, z, l)$ can be measured, e.g., using a commercially available OFDR system (some OFDR systems refer to l as an integration width).

With $R_{p \to r}^{(Raleigh)}(\lambda, z)$, we denote the Rayleigh backscatter from fiber mode $E_p$ to a counter-propagating mode $E_r$ at wavelength $\lambda$ and position z, which is well known to add incoherently and therefore is independent of the integration length l. Assuming that the Rayleigh and enhanced backscatter add incoherently as well, the total backscatter of the fiber is approximately given by $$R_{p \to r}^{(fiber)}(\lambda, z, l) \approx R_{p \to r}^{(Rayleigh)}(\lambda, z) + R_{p \to r}(\lambda, z, l). \quad (7)$$

Possible constraints on the enhanced backscatter reflectivity $R_{p \to r}(\lambda, z, l)$ are that, similar to the Rayleigh scatter $R_{p \to r}^{(Raleigh)}(\lambda, z)$, it should (a) be present at all positions z along the waveguide in order to avoid blind spots, and/or that $R_{p \propto r}(\lambda, z, l)$ should (b) be approximately independent of the integration length l, i.e., the backscatter intensity should scale linearly with the considered integration length l, and/or that, unlike the broadband Rayleigh scatter $R_{p \to r}^{(Raleigh)}(\lambda, z)$, the enhanced backscatter $R_{p \to r}(\lambda, z, l)$ should (c) preferably exist only in a well controlled range of wavelengths (in-band), which may be equal to the bandwidth of the interrogation scheme (OTDR, OFDR, etc.), to keep the required dosage of the actinic radiation and the induced additional transmission loss for the guided light as low as possible. For any given modal overlap coefficient $\mu_{p,r}$ and target function $R_{p \to r}(\lambda, z, l)$, a longitudinal refractive index distribution $\Delta n_z(z)$ that satisfies all or some of these conditions may be found by solving the approximative Eq. (5) for $\Delta n_z(z)$, e.g., using an inverse Fourier transform, and using a suitable assumption for the phase of the integral on the right hand side in Eq. (5). If $\Delta n(x, y, z)$ in Eq. (3) is not sufficiently weak, multipath interference (MPI) effects cannot be neglected and Eq. (5) may not be accurate enough for practical purposes. In this case, the more time consuming inverse scattering problem that relates the reflected and incident waves in the considered section of the waveguide in the framework of Maxwell's equations needs to be solved to find $\Delta n_z(z)$.

The enhancement in scatter of the present invention may also be understood from the well-known dependencies of back scattering and transmission loss in optical fibers. For example, others (such as Nakazawa. (in JOSA73(1983), 1175-1180) and Personick (in Bell Tech J. 56(1977), 355-366)) have shown that the power fraction lost in transmission per unit length due to Rayleigh scattering, is given by the Rayleigh scattering coefficient $\alpha_{Rayleigh}(\lambda, z)$, which is usually proportional to $\lambda^{-4}$. It is also known that the core guided, back scattering signal from a given length of fiber is proportional to $\alpha_{Raleigh}$ and to the fiber recapture fraction, which is proportional to the square of the fiber numerical aperture $NA^2$. In the case that $E_p$ is the fundamental mode of the fiber, and $E_r$ is the counterpropagating fundamental mode, we have:

$$R_{p \to r}^{(Rayleigh)}(\lambda, z) = \alpha_{Rayleigh}(\lambda, z) \left( \frac{NA}{2n_{eff}} \right)^2, \quad (8)$$

where $R_{p \propto r}^{(Raleigh)}$ is the relative fraction of light back scattered per unit length (from fiber fundamental mode $E_p$ to counter-propagating fundamental mode $E_r$), and $n_{eff}$ is the effective index of the mode. Therefore, any fiber design that increases the backscattering due to an increase in Rayleigh scattering coefficient will also increase the transmission loss (in fundamental mode $E_p$). In realistic fibers, the loss due to Rayleigh scattering is accompanied by other transmission losses. That is, the total fraction of power lost per unit length is:

$$\alpha_{fiber} = \alpha_{Rayleigh} + \alpha_{non-Rayleigh} \quad (9)$$

Here, $\alpha_{non-Rayleigh}$ is the fraction of power lost in transmission to mechanisms other than Rayleigh scattering, such as UV or IR absorption or Mie scattering. In general, a of merit may then be derived for any fiber by considering a given length of the fiber and measuring the light that is back scattered (from fiber fundamental mode $E_p$ to counter-propagating fundamental mode $E_r$) and the light that is lost in transmission (in fiber mode $E_p$) through that length. To normalize out the effect of the NA, the following figure of merit (FOM) may be computed from these measured quantities:

$$FOM = \frac{R_{p \to r}^{(fiber)}}{\alpha_{fiber} \left( \frac{NA}{2n_{eff}} \right)^2}. \quad (10)$$

The light that is backscattered, $R_{p \to r}^{(fiber)}$, may be measured using for instance optical frequency or time domain reflectometry. The total transmission loss $\alpha_{fiber}$ may be measured with standard fiber loss cut back measurements. For an ideal fiber with only Rayleigh scattering, we have FOM=1. For non ideal fibers with loss mechanisms other than Rayleigh scattering, we have FOM<1. The invention of this patent in general has FOM>1, and preferably FOM>2 or larger for at least some range of wavelengths $\lambda$.

Preferably, for some embodiments, $R_{p \to r}(\lambda, z, l)$ is considered sufficiently strong if it is more than 10 dB above the native Rayleigh scattering of the fiber. In the case of standard single mode fiber, the native Rayleigh scattering level is approximately $R_{p \to r}^{(Rayleigh)} \approx 6 \cdot 10^{-11}$/mm. Applying the decadic logarithm and multiplying with a factor of 10, we obtain $10 \log_{10}(6 \cdot 10^{-11}) = -102.22$. Since this is the same procedure used for the unit decibel (dB), it is common to denote this value as −102 "dB/mm" (or, equivalently, −72 "dB/m", due to $6 \cdot 10^{-11}$/mm=$6 \cdot 10^{-8}$/m and $10 \log_{10}(6 \cdot 10^{-8}) = -72.22$).

Regarding the total length L of the fiber, which can be of the order of meters (m) to kilometers (km), MPI can typically be neglected if $R_{p \to r}(\lambda, z, L) \cdot L < 0.01$ for all $\lambda$, i.e., for total backscattering levels below −20 dB.

Those having skill in the art will appreciate that the ability to tailor $\Delta n_z(z)$ in Eq. (5) results in a corresponding ability to tailor the amount of backscattering without significantly affecting other signal transmission and reflection properties, such as e.g., loss, nonlinearity, or mode field diameter.

To be clear, the tailored perturbation $\Delta n(x, y, z)$ should meet several requirements with respect to its transverse properties, longitudinal properties, and spectral properties. For example, $\Delta n(x, y, z)$ should induce only a minimal amount of loss for the modes $E_p$ and $E_r$ in which an interrogation signal is propagating in forward and backward direction. Also, the mode $E_r$ should recapture a maximum fraction of the additional backscattering. Additionally, the backscatter from these index perturbations should be spectrally sufficiently wide to cover the full wavelength range of the interrogation scheme (e.g., OFDR or OTDR) used to measure backscatter, even in the presence of the highest possible variations in temperature or strain that this backscattering fiber is intended to be able to measure.

Some embodiments further comprise an optical pump that operates at a wavelength that is outside of the wavelength range that is affected by the index perturbation. For example, if the index perturbation increases backscatter in a wavelength range that is between 1542.5 nm and 1557.5 nm, then the optical pump has a wavelength that is outside of that range. Such a pump signal may however produce gain within the increased back scatter range.

Spectral broadening of the backscatter signal to spectral regions that are not part of the interrogation scheme should be avoided because additional backscatter from those spectral regions does not increase the SNR but, instead, can have detrimental effects such as increased absorption or overall signal or optical pump attenuation in the fiber. Furthermore, to avoid unwanted blind spots along the fiber, there should be a sufficiently strong backscatter signal in the interrogation scan range from every fiber section that is longer than or equal to the intended spatial resolution of the interrogation scheme. Therefore, the shortest integration length, for which the backscatter enhancement persists over the full measurement (e.g., OFDR or OTDR) bandwidth, is an approximate lower bound for the achievable spatial resolution of the measurement system. Preferably, the backscatter will be greater than 10 dB above the Rayleigh scattering level to be considered sufficient for adequate interrogation. All of these properties can be ascertained by those having ordinary skill in the art from Eqs. (1-6) and the embodiments described herein.

With Eqs. (1-6) and the desired properties of a preferred embodiment of the high backscattering fiber in mind, one example of an interferometric measurement of a device under test (DUT) is explained for an OFDR interrogator with a fiber of group index $n_{group}=1.45$ and a scan range $\Delta\lambda=15$ nanometers (nm) from 1542.5 nm to 1557.5 nm. Typically, such OFDR methods measure a wide spectral range (e.g., 10 nm or more), and the impulse response in the time domain can be computed by the Fourier transform of the measured spectrum. If the original spectral data is proportional to the complex-valued reflection amplitude of the DUT, then the modulus squared of its impulse response is proportional to the reflected power in the time domain. If MPI and group velocity dispersion (i.e., the dependence of the group velocity on the wavelength) are negligible in the measured scan range, then this relative reflected power at time (t) is proportional to the reflectivity (per unit length, see the definition in Eq. (5)) of the DUT at position (z), such that:

$$z = t\frac{v_{group}}{2} = t\frac{c_0}{2n_{group}}, \quad (11)$$

where $v_{group}$ and $n_{group}$ represent the average group velocity and group index in the scan range, $c_0$ represents the speed of light in vacuum, and the factor of 2 in the denominator accounts for the fact that the light travels to position z and back, thereby doubling the distance traversed. Thus, according to the Nyquist sampling theorem, a spatial resolution of 55.2 micrometers (μm) is possible in our example:

$$\Delta z = \frac{c_0}{2n_{group}}\Delta t \approx \frac{\lambda^2}{2n_{group}\Delta\lambda} = \frac{(1550 \text{ nm})^2}{2 \cdot 1.45 \cdot 15 \text{ nm}} = 55.2 \text{ μm}. \quad (12)$$

The OFDR interrogator can achieve this resolution for a relatively short sensor length (e.g., several meters). The Nyquist sampling theorem similarly implies that longer sensing lengths require more (spectrally closer) spectral measurements in the given scan range and, therefore, longer scan times. This increases the sensitivity to any kind of fast variations, such as vibrations. To keep the measurement time and vibration sensitivity constant, the product of spatial resolution and sensing length should remain constant. In other words, longer sensing lengths can be achieved at the cost of coarser spatial resolution or increased sensitivity to vibrations.

FIGS. 1-4 show examples in the case $p=r=LP_{01}$, i.e., both the propagating signal (p) and the counter-propagating reflected signal (r) are propagating in the fundamental mode ($LP_{01}$) of a single-mode optical fiber. Hence, $R_{p \to r}$ in Eq.(5) is designated as $R_{LP_{01} \to LP_{01}}$. FIGS. 1 and 2 show a longer sensing length L=119.5 cm as compared to a shorter sensing length L=29.4 cm in FIGS. 3 and 4.

Figure 1B:
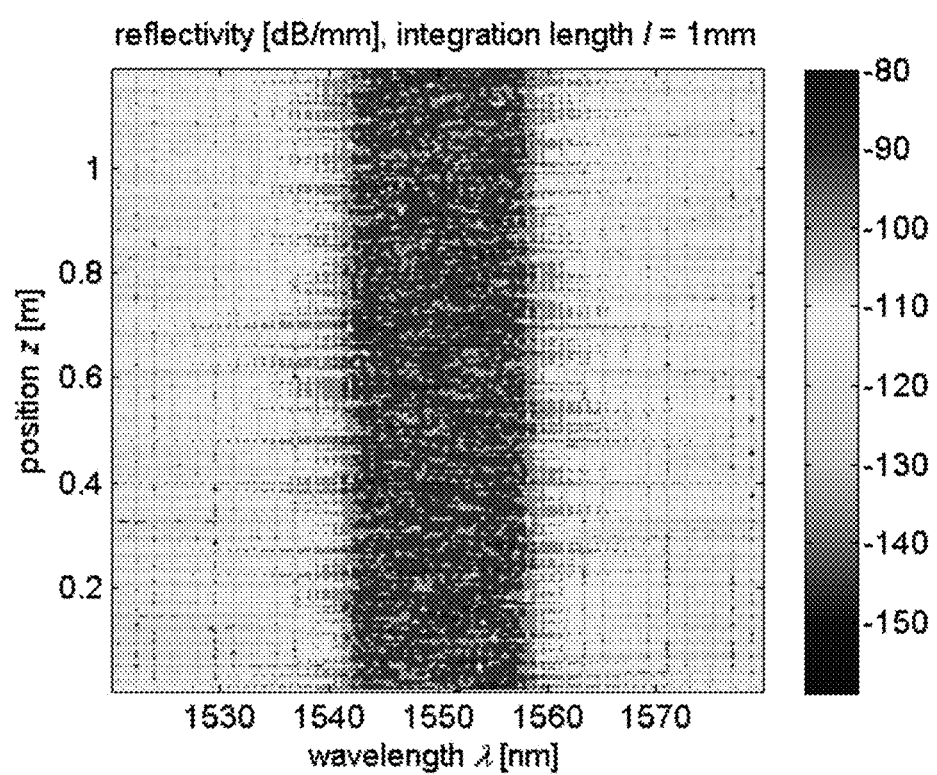

FIGS. 1A and 1B are graphs showing a plot of the reflectivity in logarithmic unit ($10 \cdot \log_{10}(R_{LP_{01} \to LP_{01}})$) from Eq. (5) with an integration length l=1 mm for one embodiment in a 119.5 cm-long fiber section with a backscatter design level of −80 dB/mm in a wavelength range of 1550±7.5 nm, i.e., $$R_{LP_{01} \to LP_{01}}(\lambda, z) \approx \frac{10^{-8}}{\text{mm}}, \quad (13)$$

$$\lambda \in [1542.5 \text{ nm}, 1557.5 \text{ nm}],$$

$$0 \le z \le 1.195 \text{ m}.$$

Figure 2A:
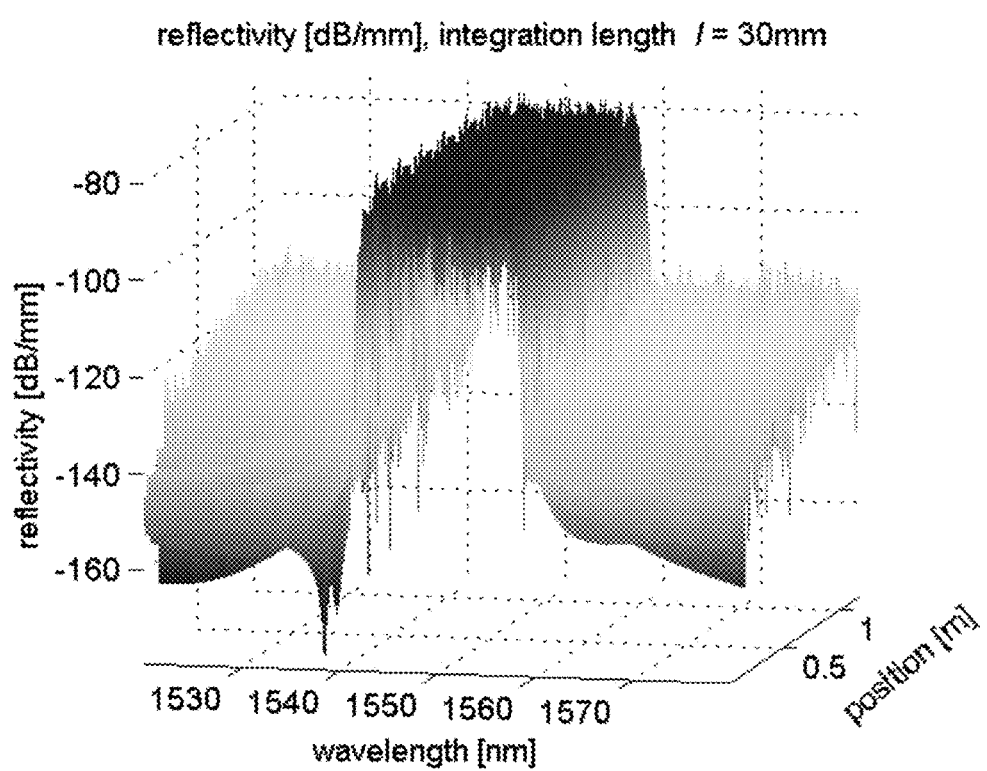
FIGS. 2A and 2B are graphs showing the reflectivity for one embodiment in which the integration length is 30 mm in a 119.5 cm-long fiber section with a design level of −80 dB backscatter per 1 mm in a wavelength range of 1550±7.5 nm.
Figure 2B:
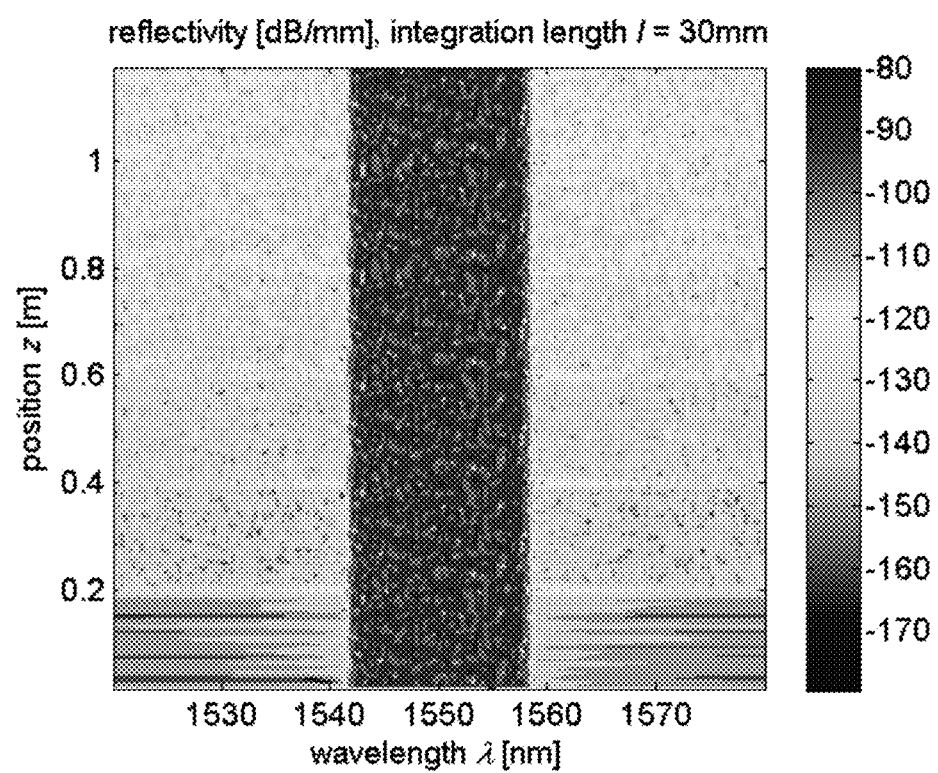

Specifically, FIG. 1A plots, in three dimensions (3D), the reflectivity (in unit dB/mm) as a function of wavelength ($\lambda$) and z-position along the fiber (in meters (m)); using an integration length l=1 mm. The shortest integration length for which the backscatter enhancement persists over the full measurement (e.g, OFDR or OTDR) bandwidth is an approximate lower bound for the achievable spatial resolution of the measurement. FIG. 1B shows the same result in a two-dimensional (2D) plot. FIGS. 2A and 2B are graphs showing reflectivity with an integration length l=30 mm, with all other parameters being equal to those of FIGS. 1A and 1B, respectively.

Figure 3A:
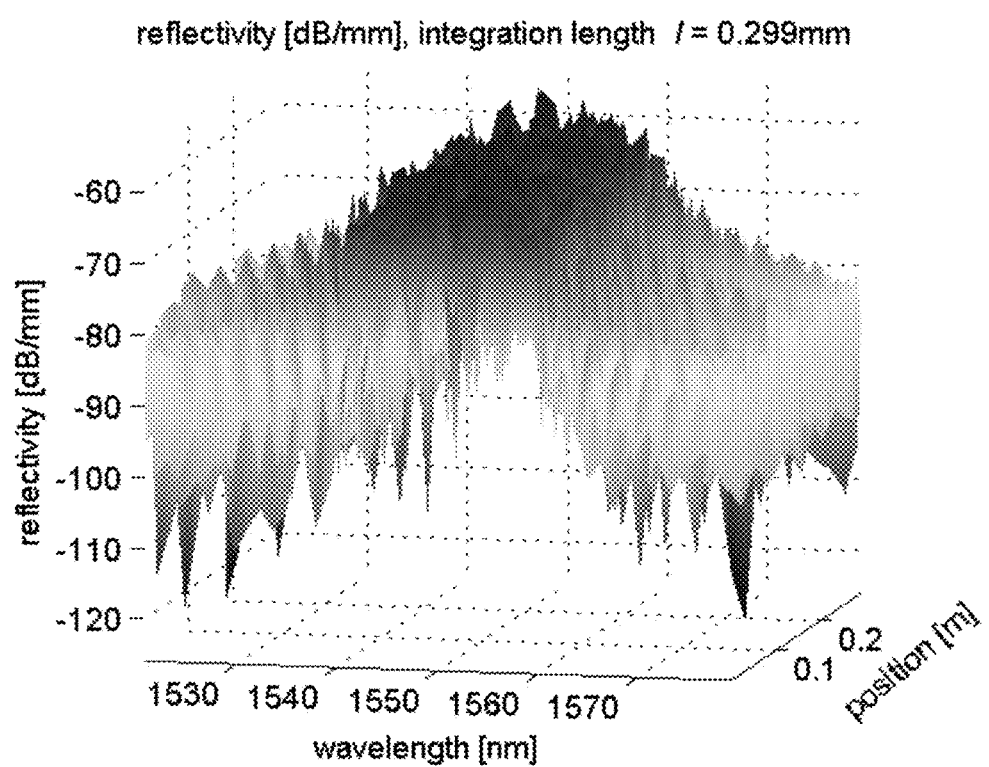
FIGS. 3A and 3B are graphs showing the reflectivity for one embodiment in which the integration length is approximately 0.3 mm (more precisely, 0.299 mm) in a 29.4 cm-long fiber section with a design level of −60 dB backscatter per 1 mm in a wavelength range of 1550±7.5 nm.
Figure 3B:
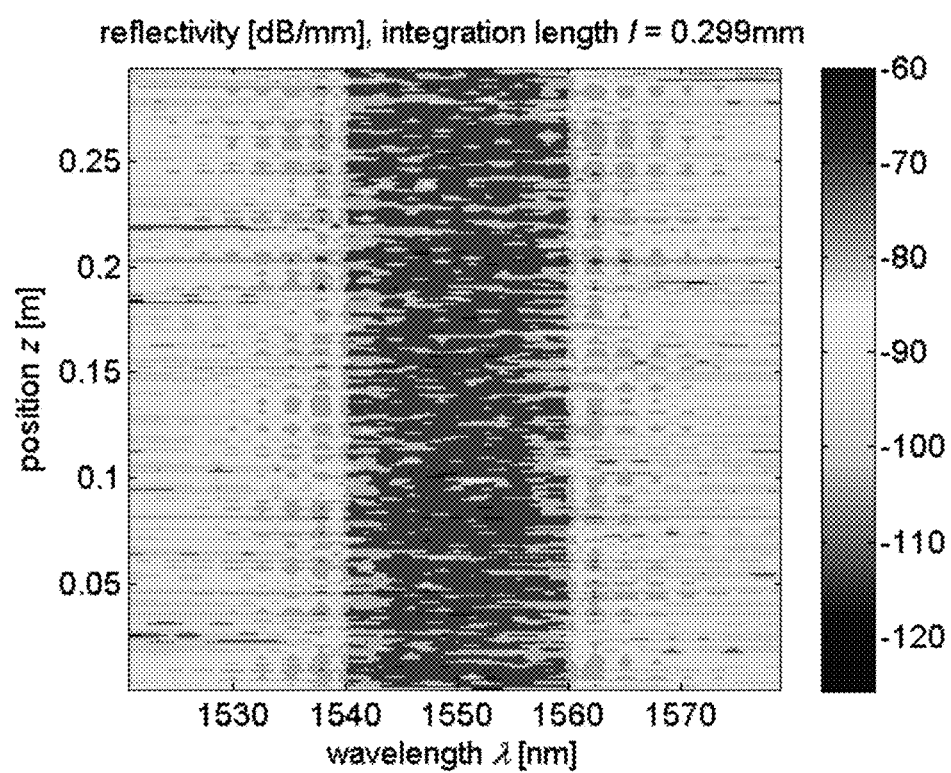

FIGS. 3A and 3B are graphs showing a plot of reflectivity with an integration length of approximately 0.3 mm (more precisely, 0.299 mm) in a 29.4 cm-long fiber section with a backscatter design level of −60 dB/mm in a wavelength range of 1550±7.5 nm, i.e., $$R_{LP_{01} \to LP_{01}}(\lambda, z) \approx \frac{10^{-6}}{mm}, \quad (14)$$

$$\lambda \in [1542.5 \text{ nm}, 1557.5 \text{ nm}],$$

$$0 \le z \le 29.4 \text{ cm}.$$

Figure 4A:
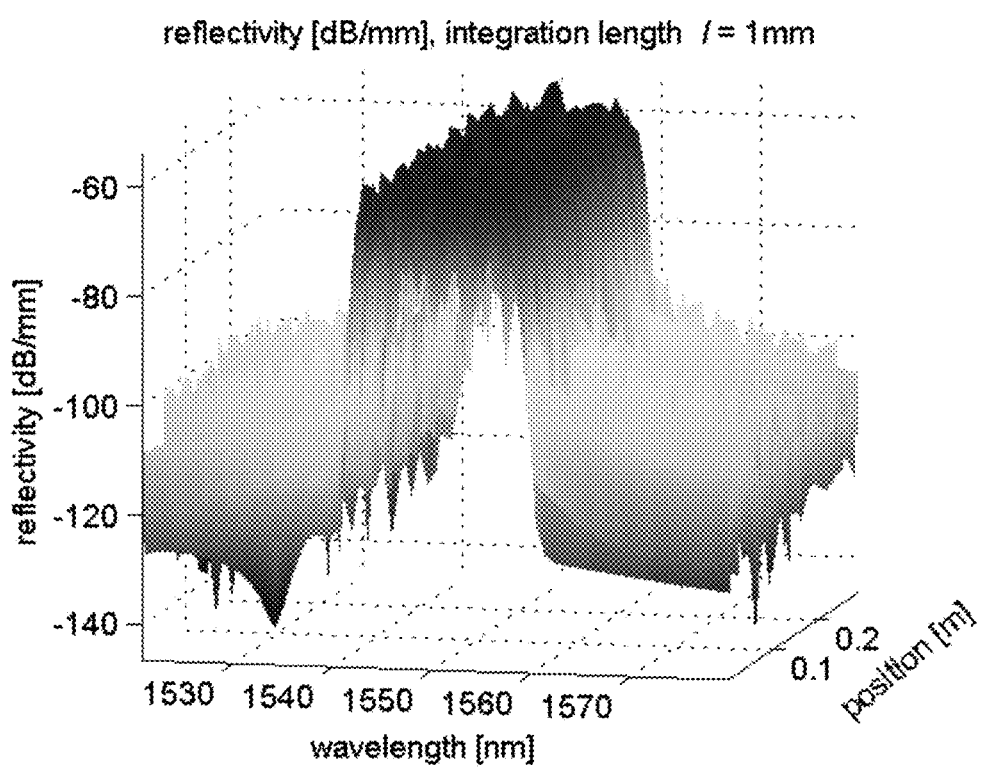
FIGS. 4A and 4B are graphs showing reflectivity for one embodiment in which the integration length is 1oam in a 29.4 cm-long fiber section with a design level of −60 dB backscatter per 1 mm in a wavelength range of 1550±7.5 nm.
Figure 4B:
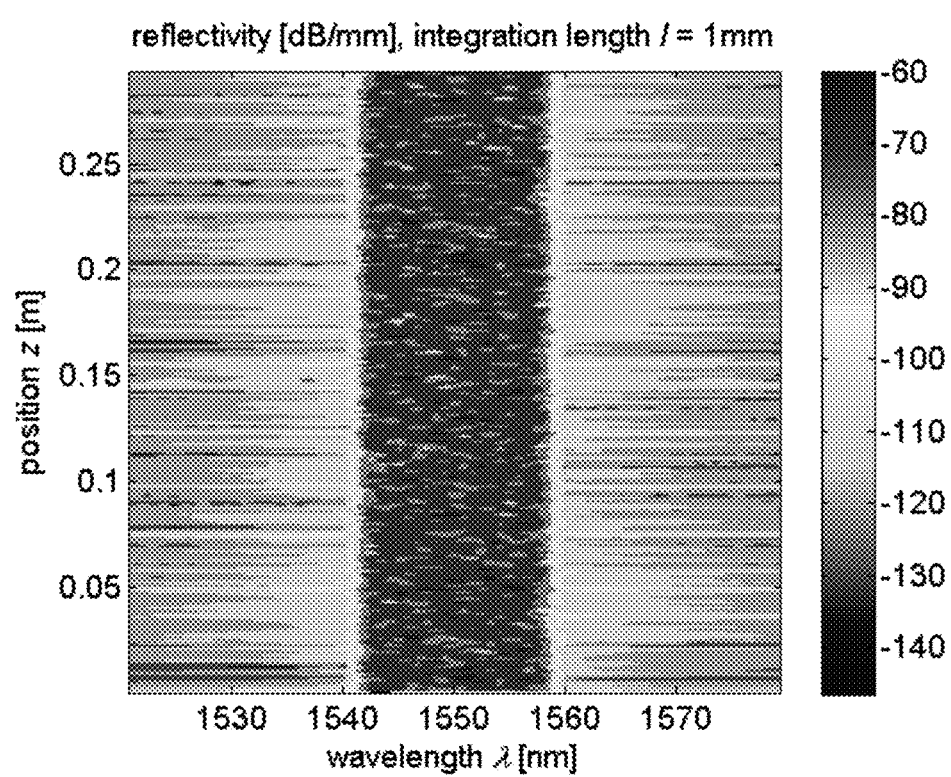

Specifically, FIG. 3A plots in 3D the reflectivity (in dB/mm) as a function of λ and z-position along the fiber, using an integration length of 0.299 mm, FIG. 3B shows the same result in a 2D plot. FIGS. 4A and 4B are graphs showing reflectivity for one embodiment in which the integration length is 1 mm, with all other parameters being equal to those of FIGS. 3A and 3B, respectively.

The setup for FIGS. 1A, 1B, 2A, and 2B includes six (6) individual 20 cm-long sections with an overlap of 1 mm between each section, thereby resulting in a fiber of length L=119.5 cm. To achieve the intended backscatter enhancement, the refractive index perturbation $\Delta n_z(z)$ (see Eq. (3)) does not need to be periodic or quasi-periodic with this period of 20 cm or 19.9 cm, respectively. In the core of the fiber, which typically has a core radius $R_{core}$ of a few micrometers (μm), the z-averaged modulus $\overline{\Delta n}(x, y)$ of the refractive index perturbations $\Delta n(x, y, z)$ in this example is $$\overline{\Delta n}(x, y) := \frac{1}{L} \int_0^L |\Delta n(x, y, z)| \, dz = 1.2 \cdot 10^{-7}, \quad (15)$$

$$x^2 + y^2 \le R_{core}^2,$$

with a sufficient variation in the local shape and curvature of $\Delta n_z(z)$ to attain an average reflection of −57 dB per 20 cm (−80 dB/mm=−20 dB/km) in the wavelength (λ) range (in-band) of approximately 15502±7.5 nm. In this calculation, we assume a coupling coefficient with modulus $|\mu_{LP_{01}-LP_{01}}| \approx 1$ in Eq. (5). To achieve the same reflectivity with fiber modes that have smaller coupling coefficients $\mu_{p,r}$, $\overline{\Delta n}$ needs to be increased inversely proportional to $|\mu_{p,r}|$.

The expected level of −80 dB/mm can be observed for a wide range of integration lengths, from l=1 mm (in FIGS. 1A and 1B) to l=30 mm (in FIGS. 2A and 2B). As people skilled in the art will appreciate, this means that the backscatter from $\Delta n(x, y, z)$ in Eq. (2) adds incoherently, as in the case of native Rayleigh scattering. Since −80 dB/mm is the same as −20 dB/km, a total length of approximately L=1 km is possible in this case without violating the above mentioned condition that the total backscattering level should be below −20 dB to avoid MPI.

FIGS. 1A and 1B show, a spatial resolution of approximately 1 mm is possible with such 20 cm-long individual sections of 15 nm bandwidth, because $R_{LP_{01} \to LP_{01}}(\lambda, z)$ does not significantly drop below the design level of −80 dB/mm within the wavelength band of interest, i.e., 1550±7.5 nm, for any length that is significantly longer than the integration length l=1 mm. In general, we define the in-band reflectivity enhancement factor $\gamma_{in-band} > 0$ as the ratio of total backscatter $R_{p \to r}^{(fiber)}$ to Rayleigh backscatter $R_{p \to r}^{(Rayleigh)}$ according to $$\gamma_{in-band}(z, l) := \frac{R_{p \to r}^{(fiber)}(\lambda_{in-band}, z, l)}{R_{p \to r}^{(Rayleigh)}(\lambda_{in-band}, z)}. \quad (16)$$

in the bandwidth of high scattering. In the example of FIGS. 1A and 1B, we have $|\lambda_{in-band} - 1550 \text{ nm}| \le 7.5$ nm, and assuming a standard single mode fiber with the typical Rayleigh scattering level $R_{p \to r}^{(Rayleigh)} = -102$ dB/mm, we have in-band values of $R_{p \to r}^{(fiber)}(\Delta_{in-band}) \approx R_{p \to r}(\Delta_{in-band})$, and $\gamma_{in-band} \approx 22$ dB. To relate the in-band and potentially unwanted out-of-band enhancement, we define the out-of-band reflectivity suppression factor $\delta_{out-of-band} > 1$ according to $$\delta_{out-of-band}(z, l) := \frac{R_{p \to r}^{(fiber)}(\lambda_{in-band}, z, l)}{R_{p \to r}^{(fiber)}(\lambda_{out-of-band}, z, l)}. \quad (17)$$

In the example of FIGS. 1A and 1B, we have $|\lambda_{out-of-band} - 1550 \text{ nm}| > 7.5$ nm, $$R_{p \to r}^{(fiber)}(\lambda_{out-of-band}) \approx R_{p \to r}^{(Rayleigh)}(\lambda_{out-of-band})$$

and $$\delta_{out-of-band} \approx 22 \text{ dB}.$$

The spatial index perturbation is reproducible along the fiber length to achieve a total sensor length that far exceeds 119.5 cm. At this moderate level of backscatter, longer sensors in which the sensor length exceeds one (1) kilometer (km) are possible without significant MPI.

The setup for FIGS. 3A, 3B, 4A, and 4B includes twelve (12) individual 25 mm-long sections with an overlap of 0.5 mm between each section, thereby resulting in a 29.4 cm-long fiber. To achieve the intended backscatter enhancement, the refractive index perturbation $\Delta n_z(z)$ (see Eq. (3)) does not need to be periodic or quasi-periodic with this period of 25 mm or 24.5 mm, respectively. The average refractive index perturbations in the core of the fiber had an average amplitude of $$\overline{\Delta n}(x, y) := \frac{1}{L} \int_0^L |\Delta n(x, y, z)| \, dz = 1.2 \cdot 10^{-6}, \quad (18)$$

$$x^2 + y^2 \le R_{core}^2,$$

with a sufficient variation in their local shape and curvature to attain an average reflection of −46 dB per 25 mm (≈−60 dB·(1/mm)≈−30 dB/m) in the same in-band range as in FIGS. 1A, 1B, 2A, and 2B. As FIGS. 3A and 3B show, a sub-mm resolution is possible with such 25 mm-long individual sections of 15 nm bandwidth, because $R_{LP_{01} \to LP_{01}}(\lambda, z)$ does not drop significantly below the design level of −60 dB/mm within the wavelength band of interest, i.e., 1550±7.5 nm, for any length that is significantly longer than the integration length l=0.3 mm.

A coarser spatial resolution loosens the above criterion for blind spots along the fiber, see FIG. 2 in comparison to FIG. 1, and see also FIG. 4 in comparison to FIG. 3. Also, those having skill in the art will appreciate that longer design lengths for individual lengths that make up the overall grating may be preferable for fabrication.

The disclosed embodiments enjoy numerous advantages as compared to other approaches. For example, many fibers are constrained by specifications other than the requirement of high backscattering. For instance, while it is possible to increase backscattering by increasing the numerical aperture (NA) or increasing Germanium (Ge) doping in a fiber, an increase in Ge doping or an increase in NA results in an optical fiber that typically cannot be optimized for other uses. For instance, a high NA fiber that is still single mode at the signal wavelengths exhibits a relatively high coupling loss, whether by mechanical connector or fusion splice, as compared to a low NA fiber, such as standard single-mode fiber used in telecommunications systems. Use of co-dopants to depress the NA of a high backscattering fiber is somewhat ineffective for improving splice and connector loss. Additionally, high NA fibers experience a relatively high transmission loss. Because transmission loss is directly related to the increased backscattering resulting from high NA, there are strict limits on the achievable loss level of such an increased-dopant fiber.

Conversely, the high backscattering fiber disclosed herein increases backscattering without substantially increasing the transmission loss or coupling loss. For instance, the index perturbations that cause the backscattering in FIGS. 1A through 4B can be introduced into low loss transmission fibers with mode fields and NA matched to standard single-mode fiber, thus resulting in high backscattering loss while providing low coupling loss and low transmission loss. The resulting fiber would exhibit transmission loss only due to the increased backscattering and only over a designated range of wavelengths.

Additionally, reduced coupling loss and transmission loss accompanied by high backscattering may be applied to fibers with other properties. For example, some fibers have specifically designed linear and nonlinear properties, such as very low or very high nonlinearity, or very low or very high group velocity dispersion.

In the disclosed high backscattering fibers, these parameters can be specifically tuned while at the some time providing a high backscattering signal. For instance, it is well known that changing the mode effective area of a single mode fiber is a way to tune the nonlinearity of the propagation. Thus, a high nonlinearity may be achieved with a reduced mode field area, and conversely, an increased mode effective area will decrease the nonlinearity of propagation. Increased nonlinearity would benefit applications that require enhanced nonlinear effects or gain from Raman, Brillouin, or parametric effects. Decreased nonlinearity would benefit applications that require propagation without nonlinear distortion.

For some embodiments, axial variation of backscatter can be introduced along a fiber. For example, backscatter can be made stronger at the distal end of the fiber, thereby counteracting the natural attenuation of the signal during propagation. The disclosed high backscatter fiber can also control the optical bandwidth of backscatter, levels of transmission loss, coupling loss, splice loss, connector loss, and mode field area. Furthermore, the disclosed high backscatter fiber can also be used in conjunction with specific active characteristics, such as optical gain or nonlinearity, which can be induced, e.g., by rare-earth dopants or Raman gain. Similarly, the disclosed fiber can specifically control dispersion or birefringence and other linear or nonlinear propagation properties.

Because of the characteristics of backscattering, the disclosed fibers can also provide controlled, intentional sensitivity to environmental conditions. For example, temperature, strain, bend, twist, $H_2$, corrosion, and other sensitivity can be provided by using materials that are intentionally sensitive to, for example, $H_2$ darkening. Other benefits include the following:

The combination of high back scattering and high precision placement of a core with respect to other cores or stress rods or the fiber axis and various multicore or microstructured fiber cross sections, including twisted and non-twisted fiber can be advantageous for certain types of sensors. For instance, shape sensing can be achieved in twisted multicore fiber. For such a fiber to be useful, the multiple cores must be placed within the fiber with great accuracy in order to maintain a certain calibration for the optical sensor. Such accurate placement requires precision machining and consolidation of the preform. If the cores have been designed for high scattering, their thermomechanical properties may not be well suited to such precise fabrication. For instance, when the Ge content of a silica core is increased, its Rayleigh back scattering will increase. However, such high Ge doped cores have lower viscosity compared to the surrounding silica, complicating the fabrication. Therefore, a means to increase the back scattering without the requirement of increased Ge content is desirable in order to achieve high precision placement of a core or cores within a fiber while still having the possibility of large back scattering.

Center wavelength of operation may have to be constrained for certain applications, thus requiring scattering for certain wavelengths, but not others. For example, very long wavelengths or other wavelengths where Rayleigh scattering is dominated by infrared (IR) loss and other scattering mechanisms. For longer wavelengths in silica fibers, typically above 4 µm, there is increased IR loss. Back scattering from Rayleigh scattering may not be sufficient due to this loss. As a result, sensors that require such long wavelengths will require additional back scattering to be useful. In another example, it may be necessary to allow loss and low back scattering propagation at one wavelength, while having high back scatter at another wavelength. Typical waveguides cannot provide such selective enhancement at a given wavelength or band of wavelengths. The modifications described herein allow for such increased back scattering over a given desired bandwidth.

Fiber lengths that include lasers, cavities or lasing are also used in some applications. Such active waveguide devices can be used for sensing or light generation. In such devices it may be necessary to increase back scattering in order to improve the lasing properties or in order to provide a monitoring signal to give information about the lasing device along its length.

Fibers in which backscatter intensity scales linearly or at least less than quadratically with the length of the fiber are important for certain sensing applications. It is known that a Rayleigh scattered optical signal scales linearly with the length of the waveguide due to the incoherent nature of the scattering. A fiber with increased scattering could also be designed to increase back scattering linearly with the length of waveguide used. Such a simple linear increase would for instance, allow for the enhanced scattering waveguide to be used with the same sorts of algorithms that would be used with Rayleigh scattering with only an increase in signal to noise ratio being available in the enhanced fiber.

Fibers in which backscatter intensity scales linearly or at least less than quadratically with the modulation induced in the fiber are of interest for some applications. Thus, the enhanced fibers would be similar to Rayleigh scattering in standard fibers which exhibit a roughly linear relationship between index modulation and scattering intensity.

The fibers of this disclosure include additional variations in refractive index, unlike those that result from thermal fluctuations. These additional variations preferably have some long range order. For example, in part of the cross section where the propagating mode intensity is highest, the index variations (also designated herein as perturbations) will preferably have little-to-no variation in the direction transverse to the optical fiber. Thus, core guided light will experience minimal overlap with radiation modes, giving rise to less transmission loss and more backscattering. The refractive index variations extended, in some embodiments, into the fiber cladding sufficiently to suppress coupling from the core to the cladding modes completely or almost completely.

Index variations may have a spatial spectrum that is peaked at one or more length scales. One example of such a length scale would be of the order of 500 nm. Such a length scale would increase scatter near a wavelength of 1550 nm in a typical single-mode fiber without increasing the scattering at other wavelengths. For some embodiments, the index variations would exhibit a primary length scale and would exhibit a non-repeating phase variation about this primary length scale. That is, at any point along the fiber, index variations with the primary length scale would be observed. However, the phase and amplitude of these refractive index variations would be random from one spatial point to another.

In yet other embodiments, the variations would repeat over some length scale much longer than the primary spatial frequency peak, such as, for example, repeating over a length scale of 1 cm or 2.5 cm, as in FIGS. 1A, 1B, 2A, and 2B, with or without gaps or overlaps of the 1 cm or 2.5 cm long sections. Alternatively the pattern can be partially periodic. Thus the same pattern (or portions of the same periodic pattern) may appear with varying phase.

In yet other embodiments, the refractive index variations would be large enough to increase backscattering, but not so large that multiple scattering (multipath interference, MPI) would affect measurements. Thus, the backscatter would be much larger than the backscattering for Rayleigh scattering while still occurring only once in the waveguide. In a preferred embodiment, the backscattering from each point along the fiber waveguide would be the maximum value consistent with the requirements of minimal sensor performance degradation due to MPI. That is, if a total backscattering level below −20 dB was required for the sensor interrogator to operate as mentioned above, the single backscattering signal at each point would be as large as possible subject to the constraint that the impact of multiple backscattering is negligible in the output signal. It is understood that this optimal scattering might require the backscattering signal to not be uniform along the fiber.

Alternatively, the induced modulation can be chosen such that it is minimal in amplitude while still obtaining the maximum possible back scattering signal.

In another embodiment, there would be two or more primary length scales for the index variations. In yet another embodiment, the backscattering signal would vary along the fiber. The backscattering signal might be the same as the native, inherent scattering for certain points along the fiber.

Some embodiments of the high-scattering optical fiber comprises a Rayleigh scattering that is greater than −99 dB/mm and a coupling loss of less than 0.2 dB (preferably, less than 0.1 dB) at a wavelength range between 1450 nm and 1650 nm, preferably between 1500 nm and 1625 nm, when coupled to a G.652-standards compliant optical fiber. Insofar as those in the optical fiber industry are familiar with the G.652 standard, further discussion of G.652 is omitted here.

Some embodiments comprise a high backscattering fiber with a backscattering power that is greater than −99 dB/mm within its operating wavelength range, and a transmission loss that is less than 10 dB/km, but preferably less than 2 dB/km, within the operating wavelength range. For such embodiments, the high backscattering fiber can further comprise a bandwidth ($\Delta\lambda$), wherein $\Delta\lambda \geq 1$ nm, and an in-band reflectivity enhancement factor ($\gamma$), wherein $\gamma \geq 10$ dB (i.e., $10 \log_{10}(\gamma) = 10$ decibels (dB)). A preferable in-band center wavelength ($\lambda_0$) would be:

$$950 \text{ nm} < \lambda_0 < 1700 \text{ nm}.$$

More preferably, in the range of:

$$1500 \text{ nm} < \lambda_0 < 1625 \text{ nm},$$

the high backscattering fiber would exhibit a Rayleigh backscatter ($R_{p \to r}^{(Rayleigh)}$) of:

$$-110 \text{ dB/mm} < R_{p \to r}^{(Rayleigh)}(\lambda_0) < -90 \text{ dB/mm}.$$

In its broadest sense, some embodiments comprise an optical fiber with an effective index of $n_{eff}$, a numerical aperture of NA, a scatter of $R_{p \to r}^{(fiber)}$, a total transmission loss of $\alpha_{fiber}$, an in-band range greater than 1 nm, and a figure of merit (FOM) within the in-band range, where FOM>1. As noted above, the FOM is defined as:

$$FOM = \frac{R_{p \to r}^{(fiber)}}{\alpha_{fiber} \left( \frac{NA}{2 n_{eff}} \right)^2}.$$

More narrowly, the in-band range where the FOM>1 is preferably between approximately 1500 nm and approximately 1625 nm. Also, for some embodiments in which the FOM>1, the optical fiber comprises a coupling loss that is less than 0.2 dB in the in-band range when coupled to a G.652-standard compliant optical fiber. For other embodiments where FOM>1, the optical fiber comprises a total backscatter that is greater than −99 dB/mm within the in-band range and a transmission loss that is less than 2 dB/km within the in-band range. For yet other embodiments where FOM>1, the optical fiber has a length that is greater than 20 cm. Although an FOM>1 is described, it should be appreciated that in some embodiments it is preferable to have FOM>2. For certain applications, it should be appreciated that a higher level of loss (e.g., 10 dB/km to 500 dB/km) can be tolerated.

Although exemplary embodiments have been shown and described, it will be clear to those of ordinary skill in the art that a number of changes, modifications, or alterations to the disclosure as described may be made. For example, those having skill in the art understand how to induce index perturbations using tailored actinic radiation, such as UV, gamma, or femtosecond infrared (IR), which are all known methods for modifying refractive indices of silica or other glasses. Those having skill in the art will also understand that the index perturbations are inducible using an interference pattern from two actinic beams, by using a phase mask with a tailored modulation of its phase, or by using a point-by-point system with a tailored modulation of the writing beam intensity along the fiber. The tailored modulations are derivable from the intended, optical spectrum of the backscatter of the optical fiber, as explained above with reference to the equations and FIGS. 1A through 4B. Also, while a counter-propagating mode (r) is described, it should be appreciated that this disclosure is equally applicable to co-propagating modes for which $+n_{eff,r}$ can simply be replaced with $-n_{eff,r}$ in Eq. (5). It should be appreciated that backscattering can be measured using either OTDR or OFDR techniques. For OFDR, index-matching the rear end of the waveguide or fiber is preferable to minimize measurement errors that are induced by MPI with discrete reflections from the rear end. Those having skill in the art will appreciate that the disclosed high backscattering fiber can include polymers, silicates, silica, fluorides, chalcogenide, etc., and that the structure of these fibers can be solid or micro-structured, including photonic crystal fibers, photonic bandgap fibers, hollow core fibers, etc., or any combinations thereof. For instance, a hollow core fiber that is filled with a certain gas, fluid, plasma, or another solid material. Also, it should be appreciated that, for some embodiments, the high backscattering fibers should have induced modulations that are minimal in amplitude while still obtaining the maximum possible backscattering signal. Furthermore, although optical fibers are shown in example embodiments, it should be appreciated that the high backscattering is applicable to all waveguides. Lastly, unless designated otherwise, either expressly or by context, light is defined to mean visible light, UV radiation, or IR radiation.

All changes, modifications, and alterations should be seen as being within the scope of the disclosure.

What is claimed is:

1. An optical fiber having a modified refractive index caused by applying a spatial pattern that creates a refractive index perturbation, the optical fiber comprising:
    an effective index of $n_{eff}$;
    a numerical aperture of NA;
    a scatter of $R_{p \to r}^{(fiber)}$;
    a total transmission loss of $\alpha_{fiber}$;
    an in-band range greater than 1 nm; and
    a figure of merit (FOM) in the in-band range, FOM>1, the FOM being defined as:

$$FOM = \frac{R_{p \to r}^{(fiber)}}{\alpha_{fiber}\left(\frac{NA}{2n_{eff}}\right)^2}.$$

2. The optical fiber of claim 1, the in-band range being between approximately 1450 nm and approximately 1650 nm.

3. The optical fiber of claim 2, further comprising:
    a coupling loss less than 0.2 dB in the in-band range when coupled to a G.652-standard compliant optical fiber.

4. The optical fiber of claim 2, further comprising:
    a total backscatter greater than −99 dB/mm within the in-band range; and
    a transmission loss less than 2 dB/km within the in-band range.

5. The optical fiber of claim 2, further comprising:
    a total backscatter greater than −99 dB/mm within the in-band range; and
    a transmission loss less than 10 dB/km within the in-band range.

6. The optical fiber of claim 4, further comprising:
    a coupling loss less than 0.2 dB in the in-band range when coupled to a G.652-standard compliant optical fiber.

7. The optical fiber of claim 1, further comprising a length that is greater than 20 cm.

8. The optical fiber of claim 1, the FOM being greater than 2.

9. The optical fiber of claim 1, further comprising:
    an out-of-band range; and
    an optical pump having a wavelength in the out-of-band range.

10. A high backscattering optical fiber having a modified refractive index caused by applying a spatial pattern that creates a refractive index perturbation, the high backscattering fiber comprising:
    an operating wavelength range;
    a total backscatter greater than −99 dB/mm within the operating wavelength range; and
    a transmission loss less than 2 dB/km within the operating wavelength range.

11. The high backscattering fiber of claim 10, further comprising:
    a bandwidth ($\Delta\lambda$), wherein $\Delta\lambda \geq 1$ nm;
    an in-band reflectivity enhancement factor ($\gamma_{in\text{-}band}$), wherein $\gamma_{in\text{-}band} \geq 10$ dB; and
    an out-of-band reflectivity suppression factor ($\delta_{out\text{-}of\text{-}band}$), wherein $\delta_{out\text{-}of\text{-}band} \geq 2$ dB.

* * * * *